United States Patent [19]

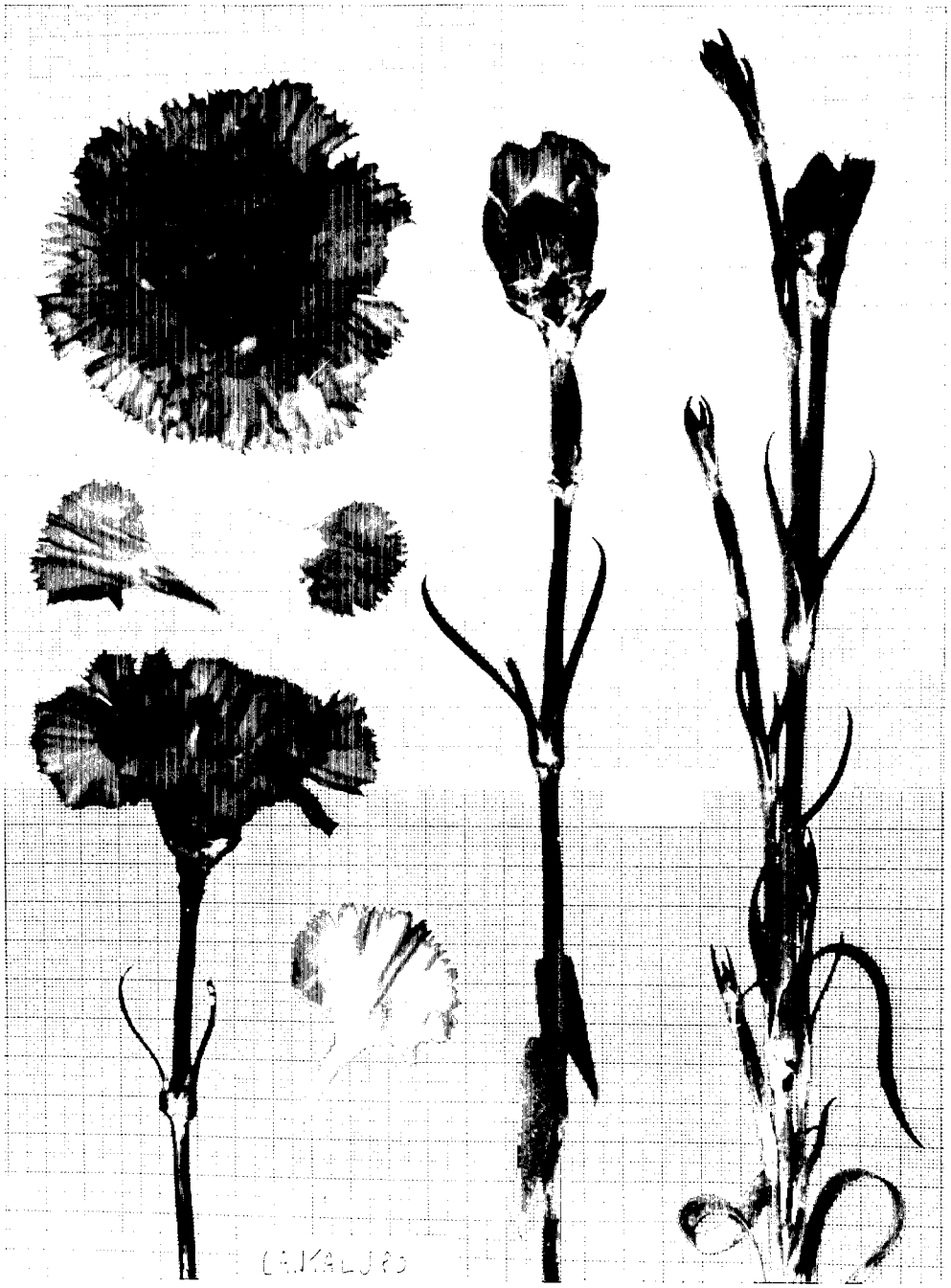

Nobbio

[11] Patent Number: Plant 5,763

[45] Date of Patent: Jul. 8, 1986

[54] CARNATION NAMED CANTALUPO

[76] Inventor: Giacomo Nobbio, Strada Villetta 5, San Remo, Imperia, Italy

[21] Appl. No.: 600,827

[22] Filed: Apr. 16, 1984

[51] Int. Cl.[4] ..... A01H 5/00

[52] U.S. Cl. ..... Plt./73

[58] Field of Search ..... Plt./73

*Primary Examiner*—James R. Feyrer

*Attorney, Agent, or Firm*—Charles W. Rummler

[57] ABSTRACT

A new variety of carnation plant particularly distinguished by its unifloral production of a double type of flower having a bright red coloration of monochrome distribution and numerous petals with sharply serrated margins, the blooms being carried on strong, upright stems of medium length and having good endurance as a cut flower and suitability for shipment.

1 Drawing Figure

BACKGROUND OF THE NEW PLANT

This new carnation plant originated at San Remo, Italy, in 1979 as a result of my breeding efforts to produce carnations particularly suitable for commercial greenhouse production of cut flowers having good qualities of stability and endurance for shipment. This new carnation variety originated in 1979 as the result of my crossing plants maintained by me for breeding purposes, the seed parent having flowers of generally rose coloration and the pollen parent being an unnamed variety which is also rose in color. After repeated trials of propagation by means of cuttings, the distinctive characteristics of my new plant held true from generation to generation and appeared to be firmly fixed, whereupon the new plant was deemed suitable for commercial propagation.

DESCRIPTION OF THE DRAWING

My new carnation cultivar is illustrated by the accompanying full color photographic drawing, which shows the inflorescence of a typical plant of the new variety, the view including buds in various stages of opening, as well as a face view and a side view of a fully opened flower, together with specimens of both pinched and unpinched stems and the flower petals. The colors shown are believed to be as close as is reasonably possible to obtain by conventional photographic procedures and consideration of specimen display as shown.

DESCRIPTION OF THE NEW PLANT

The following is a detailed description of my new carnation cultivar based upon observation of plants grown under conventional greenhouse procedures, the color designations being according to The R.H.S. Colour Chart published by The Royal Horticultural Society of London, England.

THE PLANT

Origin: Seedling.

Parentage:

*Seed parent.*—Unnamed Variety U.S. Plant Pat. No. 8,163.

*Pollen parent.*—Unnamed Variety U.S. Plant Pat. No. 8,884, the parent plants being among those maintained by me for breeding purposes.

Classification:

*Botanic.*—*Dianthus caryophyllus.*

*Commercial.*—Greenhouse carnation for cut flowers.

Form: Herbaceous with stems of medium height, having a total length of seven internodes immediately under the calyx.

Branching: Medium. The primary stem arising from a rooted cutting is pinched at about 10 or 12 cm. from the base when the stem has reached a height of about 30 cm. This is done to promote the growth of 4 or 5 shoots, each of which becomes a full length terminal flowering stem. These secondary stems will branch in the normal way and each of the branches may be allowed to produce a terminal flower or the entire secondary stem may be suitably pruned depending upon the desired length for its terminal flower.

Foliage:

*Quantity.*—Moderate.

*Leaf size.*—Moderate, of medium length and generally broad.

*Shape.*—Linear with entire margins and acuminate apex.

*Texture.*—Smooth.

*Color.*—Green.

*Stem length.*—Medium, with a total of seven internodes immediately under the flower.

*Color.*—Dark Green.

THE BUD

Size: Medium.

Shape: Ovoid immediately before sepals divide.

Sepals:

*Condition.*—Upstanding and displaying a red coloration on the upper inside portion.

Calyx:

*Shape.*—Bell-shaped.

*Length.*—Long.

*Size.*—Moderate.

*Splitting.*—On rare occasions, the calyx may split.

*Aspect.*—Smooth.

THE FLOWER

Blooming habit: Continuous.

Size of bloom: Large.

Borne: Singly on strong, upright pedicels.

Shape: Generally symmetrical with cupule slightly flattened in center.

Petalage:

*Number.*—More than 80, each with serrated margin.

*Color.*—Between R.H.S. 43B and R.H.S. 44B.

*Color distribution.*—Monochrome.

*Texture.*—Soft.

*Appearance.*—Satiny.

*Persistence.*—Good; the petals hang on and dry.

Lasting quality and suitability for shipment: Good.

REPRODUCTIVE ORGANS

Androecium: Absent during the winter period.

Styles:

*Number.*—More than two.

Stigma: Surface is smooth.

Ovary: Ovoid in shape.

The present variety of carnation is clearly distinguished from all of the other commercially available carnations. In particular, in comparison with the "Oscar" variety, the new plant is distinguished by the greater size of its flower when in complete bloom and its well balanced and stable characteristics.

I claim:

1. A new and distinct variety of carnation cultivar, substantially as herein shown and described, characterized by its large, double flower of bright red color, the color of the petals being of monchrome distribution, and the flowers being borne singly on strong, upright stems.

* * * * *

UNITED STATES PATENT AND TRADEMARK OFFICE

CERTIFICATE OF CORRECTION

PATENT NO. : Plant 5,763

DATED : July 8, 1986

INVENTOR(S) : Giacomo Nobbio

It is certified that error appears in the above-identified patent and that said Letters Patent are hereby corrected as shown below:

Column 1, line 44, delete "U.S. Plant Pat.".

Column 1, line 46, delete "U.S. Plant Pat.".

Signed and Sealed this

Twenty-first Day of October, 1986

[SEAL]

*Attest:*

DONALD J. QUIGG

*Attesting Officer*

*Commissioner of Patents and Trademarks*